United States Patent
Wolf et al.

(10) Patent No.: US 9,851,418 B2
(45) Date of Patent: Dec. 26, 2017

(54) DIAMOND MAGNETOMETER

(71) Applicants: Philipp Neumann, Stuttgart (DE); Jörg Wrachtrup, Stuttgart (DE)

(72) Inventors: Thomas Wolf, Stuttgart (DE); Philipp Neumann, Stuttgart (DE); Jörg Wrachtrup, Stuttgart (DE)

(73) Assignee: Element Six Technologies Limited, Didcot, Oxfordshire (GB)

( * ) Notice: Subject to any disclaimer, the term of this patent is extended or adjusted under 35 U.S.C. 154(b) by 0 days.

(21) Appl. No.: 14/946,912

(22) Filed: Nov. 20, 2015

(65) Prior Publication Data
US 2017/0146615 A1   May 25, 2017

(51) Int. Cl.
*G01R 33/032* (2006.01)
*G01R 33/24* (2006.01)
*H03B 17/00* (2006.01)
*G01N 21/64* (2006.01)

(52) U.S. Cl.
CPC ....... *G01R 33/032* (2013.01); *G01N 21/6402* (2013.01)

(58) Field of Classification Search
CPC .... G01R 33/032; G01R 33/24; G01R 33/307; H03B 17/00
USPC ............. 324/244, 244.1, 345; 331/94.1
See application file for complete search history.

(56) References Cited

U.S. PATENT DOCUMENTS

2014/0247094 A1 * 9/2014 Englund ............. H03B 17/00
331/94.1

OTHER PUBLICATIONS

Hari, R. & Salmelin, R. "Magnetoencephalography: From SQUIDs to neuroscience: Neuroimage 20th Anniversary Special Edition" NeuroImage, 61, 2, 386-396 (2012).
Gaffney, C. "Detecting Trends in the Prediction of the Buried Past: A Review of Geophysical Techniques in Archaeology" Archaeometry 50, 2, 313-336 (2008).
Drung, D. et al. "Highly Sensitive and Easy-to-Use SQUID Sensors" IEEE Trans. Appl. Supercond. 17, 2, 699-704 (2007).
Dang, H. B., Maloof, A. C. & Romalis, M. V. "Ultrahigh sensitivity magnetic field and magnetization measurements with an atomic magnetometer." Appl. Phys. Lett. 97, 151110, 1-3, (2010).
Ripka, P. & Janosek, M. "Advances in Magnetic Field Sensors" IEEE Sens. J. 10, 6, 1108-1116 (2010).
(Continued)

*Primary Examiner* — Arleen M Vazquez
*Assistant Examiner* — Neel Shah
(74) *Attorney, Agent, or Firm* — Armstrong Teasdale LLP

(57) ABSTRACT

A magnetometer comprising:
a sensor formed of diamond material and comprising a plurality of spin centers;
a microwave source configured to subject the plurality of spin centers to microwave pulses;
a light source configured to subject the plurality of spin centers to light pulses; and
a detector configured to detect a fluorescent output signal emitted from the plurality of spin centers,
wherein the magnetometer is configured to integrate the fluorescent output signal over a signal averaging time and process the fluorescent output signal such that a standard deviation of the fluorescent output signal decreases with the square root of the signal averaging time over a time period which spans at least two orders of magnitude in the signal averaging time to achieve a standard deviation of less than 100 picotesla.

20 Claims, 3 Drawing Sheets

(56) References Cited

OTHER PUBLICATIONS

Rugar, D., Yannoni, C. S. & Sidles, J. A. "Mechanical detection of magnetic resonance" Nature 360, 563-566 (1992).

Degen, C.L. et al. "Nanoscale magnetic resonance imaging" Proc. Natl. Acad. Sci. 106, 5, 1313-1317 (2009).

Huber, M. E. et al. "Gradiometric micro-SQUID susceptometer for scanning measurements of mesoscopic samples" Rev. Sci. Instrum, 79, 053704, 1-7, (2008).

Balasubramanian, G. et al. "Nanoscale imaging magnetometry with diamond spins under ambient conditions" Nature 455, 648-651 (2008).

Doherty, M. W. et al. "The nitrogen-vacancy colour centre in diamond" Phys. Rep. 528, 1, 1-45 (2013).

Acosta, V. M. et al. "Temperature Dependence of the Nitrogen-Vacancy Magnetic Resonance in Diamond" Phys. Rev. Lett. 104, 070801, 1-4, (2010).

Doherty, M. W. et al. "Measuring the defect structure orientation of a single NV-centre in diamond" New J. Phys. 16, 063067 (2014).

Maze, J. R. et al. "Nanoscale magnetic sensing with an individual electronic spin in diamond" Nature, 455, 644-647 (2008).

Acosta, V. et al. "Diamonds with a high density of nitrogen-vacancy centers for magnetometry applications" Phys. Rev. B 80, 115202, 1-15, (2009).

Le Sage, D. et al. "Efficient photon detection from color centers in a diamond optical waveguide" Phys. Rev. B, 85, 121202(R), 1-4, (2012).

Jiang, L et al. "Repetitive Readout of a Single Electronic Spin via Quantum Logic with Nuclear Spin Ancillae" Science 326, 267-272 (2009).

Neumann, P. et al. "Single-Shot Readout of a Single Nuclear Spin" Science, 329, 542-544 (2010).

Acosta, V. M. et al. "Broadband magnetometry by infrared-absorption detection of nitrogen-vacancy ensembles in diamond" Appl. Phys. Lett., 97, 174104, 1-3 (2010).

Jensen, K. et al. "Cavity-Enhanced Room-Temperature Magnetometry Using Absorption by Nitrogen Vacancy Centers in Diamond" Phys. Rev. Lett. 112, 160802, 1-5 (2014).

Chin, A. W., Huelga, S. F. & Plenio, M. B. "Quantum Metrology in Non-Markovian Environments" Phys. Rev. Lett. 109, 233601 (2012).

Clevenson, H. et al. "Broadband Magnetometry and Temperature Sensing with a Light Trapping Diamond Waveguide" ArXiv:1406.5235v1, Cond-Mat Physicsquant-Ph, 1-8, (2014).

Balasubramanian, G. et al. "Ultralong spin coherence time in isotopically engineered diamond" Nature Materials, 8, 383-387 (2009).

Cummins, H. K., Llewellyn, G. & Jones, J. A. "Tackling systematic errors in quantum logic gates with composite rotations" Phys. Rev. A, 67, 042308, 1-7, (2003).

Breiland, W. G., Brenner, H. C. & Harris, C. B. "Coherence in multilevel systems. I. Coherence in excited states and its application to optically detected magnetic resonance in phosphorescent triplet states" J. Chem. Phys. 62, 3458-3475 (1975).

Naydenov, B. et al. "Dynamical decoupling of a single-electron spin at room temperature" Phys. Rev. B, 83, 081201 (R), 1-4 (2011).

Lange, G. de, Wang, Z. H., Ristè, D., Dobrovitski, V. V. & Hanson, R. "Universal dynamical decoupling of a single solid-state spin from a spin bath" Science, 330, 60-63 (2010).

Neumann, P. et al. "Quantum register based on coupled electron spins in a room-temperature solid" Nat. Phys. 6, 249-253 (2010).

Mamin, H. J. et al. "Nanoscale Nuclear Magnetic Resonance with a Nitrogen-Vacancy Spin Sensor" Science 339, 557-560 (2013).

Pham, L. M. et al., "Enhanced solid-state multispin metrology using dynamical decoupling" Phys. Rev. B 86, 045214 (2012).

Said, R., Berry, D. & Twamley, J. "Nanoscale magnetometry using a single-spin system in diamond" Phys. Rev. B 83, 125410, 1-7 (2011).

Waldherr, G. et al. "High-dynamic-range magnetometry with a single nuclear spin in diamond" Nat. Nanotechnol. 7, 105-108 (2012).

* cited by examiner

DIAMOND MAGNETOMETER

FIELD OF INVENTION

The present invention relates to a diamond magnetometer configured to be highly sensitive to very small magnetic fields.

BACKGROUND OF INVENTION

Magnetic sensors find application in various areas of science and technology. Persistent efforts have led to the development of new, highly sensitive magnetic sensors as well as the improvement of existing technologies. Useful background information can be found in the following references:

Hari, R. & Salmelin, R. Magnetoencephalography: From SQUIDs to neuroscience: Neuroimage 20th Anniversary Special Edition. *NeuroImage* 61, 386-396 (2012);

Gaffney, C. Detecting Trends in the Prediction of the Buried Past: A Review of Geophysical Techniques in Archaeology. *Archaeometry* 50, 313-336 (2008);

Drung, D. et al. Highly Sensitive and Easy-to-Use SQUID Sensors. *IEEE Trans. Appl. Supercond.* 17, 699-704 (2007);

Dang, H. B., Maloof, A. C. & Romalis, M. V. Ultrahigh sensitivity magnetic field and magnetization measurements with an atomic magnetometer. *Appl. Phys. Lett.* 97, 151110 (2010);

Ripka, P. & Janosek, M. Advances in Magnetic Field Sensors. *IEEE Sens. J.* 10, 1108-1116 (2010)].

Improving sensitivity has been a strong motivation for development of subfemtotesla magnetometers. However, due to the $1/r^3$ decay of magnetic dipolar fields, sensor size is a critical further parameter. Consequently, a number of approaches are striving for high sensitivity in combination with reduced sensor sizes:

Rugar, D., Yannoni, C. S. & Sidles, J. A. Mechanical detection of magnetic resonance. *Nature* 360, 563-566 (1992);

Degen, C. L., Poggio, M., Mamin, H. J., Rettner, C. T. & Rugar, D. Nanoscale magnetic resonance imaging. *Proc. Natl. Acad. Sci.* 106, 1313-1317 (2009)

Huber, M. E. et al. Gradiometric micro-SQUID susceptometer for scanning measurements of mesoscopic samples. *Rev. Sci. Instrum.* 79, 053704 (2008);

Balasubramanian, G. et al. Nanoscale imaging magnetometry with diamond spins under ambient conditions. *Nature* 455, 648-651 (2008).

FIG. 1d compares magnetic field sensitivities and characteristic sizes for various implementations restricted to room-temperature sample and far field techniques. In essence, the graph shows that small sensors with subpicotesla sensitivity have not been realized prior to the present invention.

The favourable material properties of diamond as well as the optical and spin properties of nitrogen vacancy (NV) defect centres allow for optical polarization, manipulation and readout of its spin state [Doherty, M. W. et al. The nitrogen-vacancy colour centre in diamond. *Phys. Rep.* 528, 1-45 (2013)]. This opens new ways for the implementation of robust solid state sensors for a variety of quantities [Acosta, V. M. et al. Temperature Dependence of the Nitrogen-Vacancy Magnetic Resonance in Diamond. *Phys. Rev. Lett.* 104, 070801 (2010); Doherty, M. W. et al. Measuring the defect structure orientation of a single NV-centre in diamond. *New J. Phys.* 16, 063067 (2014)]. In particular as magnetic field sensors, NV-based approaches offer opportunity for detection of magnetic field signals both with high spatial accuracy (nanometer) as well as high field sensitivity [Maze, J. R. et al. Nanoscale magnetic sensing with an individual electronic spin in diamond. *Nature* 455, 644-647 (2008)]. In addition to the utilization of individual electronic spins in diamond material, it is also known to utilize ensembles of NV centers such as described in Acosta, V. et al. "Diamonds with a high density of nitrogen-vacancy centers for magnetometry applications" *Phys. Rev. B* 80, 115202 (2009). While this approach sacrifices the potential atomic scale resolution of single spin magnetometers it has the potential of gaining higher field sensitivity with still smaller sensor dimensions than e.g. atomic vapour-based designs.

Magnetic field detection is based on ground state Zeeman shifts of spin sublevels of NV centres $\Delta E = \gamma \hbar B$, where $\gamma$ is the gyromagnetic ratio of the electron spin and B is the field to be measured. $\Delta E$ is best determined by exploiting coherent control of the electronic spin state of the NV centres in its ground state (FIG. 1a-b). In essence the spin acquires a phase $\phi = \gamma \cdot B \cdot T_\phi$ during sensing time $T_\phi$ (B is the averaged field) in Ramsey or spin echo-type measurements [see, for example, Taylor, J. M. et al. High-sensitivity diamond magnetometer with nanoscale resolution. *Nat. Phys.* 4, 810-816 (2008)]. Optical excitation with a laser pulse concludes a single field evaluation step by invoking spin state dependent fluorescence and reinitializing the spin state via the spin selective singlet decay of the NV centers. In essence, the fluorescence response of the system S is modulated with sin(B).

It is an aim of embodiments of the present specification to enhance the sensitivity of magnetic field measurements with ensembles of spin centres and in particular to provide a magnetometer which has an improved combination of small size and high sensitivity (i.e. lower magnetic field strength measurement capability) when compared to prior art magnetometers as illustrated in FIG. 1d.

SUMMARY OF INVENTION

A diamond magnetometer comprises the following basic components:
- a sensor formed of diamond material and comprising a plurality of spin centres;
- a microwave source configured to subject the plurality of spin centres to microwave pulses;
- a light source configured to subject the plurality of spin centres to light pulses; and
- a detector configured to detect a fluorescent output signal emitted from the plurality of spin centres.

One would expect that the sensitivity of such a magnetometer could be improved by simply integrating the acquired fluorescent output signal over longer time periods. However, it has been found that when this is done using such a magnetometer, non-white noise in the device, such as from the microwave source and/or light source, prevents significant and progressive improvement in magnetic sensitivity with increasing signal integration time (see top line in FIG. 3e). The present inventors have thus developed signal processing methodologies as described in this specification to provide a diamond magnetometer which has a magnetic sensitivity which scales with signal integration time. Specifically, the diamond magnetometer is configured to integrate the fluorescent output signal over a signal averaging time and process the fluorescent output signal such that a standard deviation of the fluorescent output signal decreases with the square root of the signal averaging time over a time period which spans at least two, three, four, five, or even six orders of magnitude in the signal averaging time to achieve a standard deviation of less than 100 picotesla, 10 picotesla, 1 picotesla, 0.1 picotesla, or 0.01 picotesla (see middle line in FIG. 3e) and extrapolating to longer integration times even subfemtotesla sensitivity can be realized.

In preferred embodiments the standard deviation of the fluorescent output signal decreases linearly with the square root of the signal averaging time (see middle line in FIG. 3e) and thus follows the aspired scaling behaviour (see bottom line in FIG. 3e). According to requirements of the application, the signal averaging time may be at least 0.1 seconds, 1 second, 10 seconds, 100 seconds or more and the standard deviation of the fluorescent output signal decreases with the square root of the signal averaging time over this time period thus achieving sensing of very low magnetic fields such as those achieved using vapour cells and SQUIDS but in a small, compact, robust solid state magnetometer device (see FIG. 1d).

According to preferred configurations, the magnetometer is configured to process the fluorescent output signal by filtering both optical and microwave noise to produce a filtered signal $S_D$ having a magnetic sensitivity expressed as the standard deviation over time which scales as a function of the square root of the signal averaging time. The magnetometer can be configured to filter both optical and microwave noise by combining multiple pulse referencing steps to determine the filtered signal $S_D$. For example, the magnetometer can be configured to measure the fluorescent output signal over a plurality of discrete, non-continuous time frames and combine the plurality of discrete, non-continuous measurements to generate the filtered signal $S_D$. The filtered signal $S_D$ can be generated by taking a read-out measurement during a first part of a laser pulse, taking a reference measurement during a second part of the laser pulse, repeating the read-out and reference measurements for a subsequent laser pulse, and then calculating the filtered signal $S_D$ using the read-out measurements and the reference measurements from both laser pulses thus accounting for both laser pulse variations and also microwave variations between the laser pulses (see FIG. 3).

BRIEF DESCRIPTION OF THE DRAWINGS

For a better understanding of the present invention and to show how the same may be carried into effect, embodiments of the present invention will now be described by way of example only with reference to the accompanying drawings, in which.

DETAILED DESCRIPTION

Figure 1:
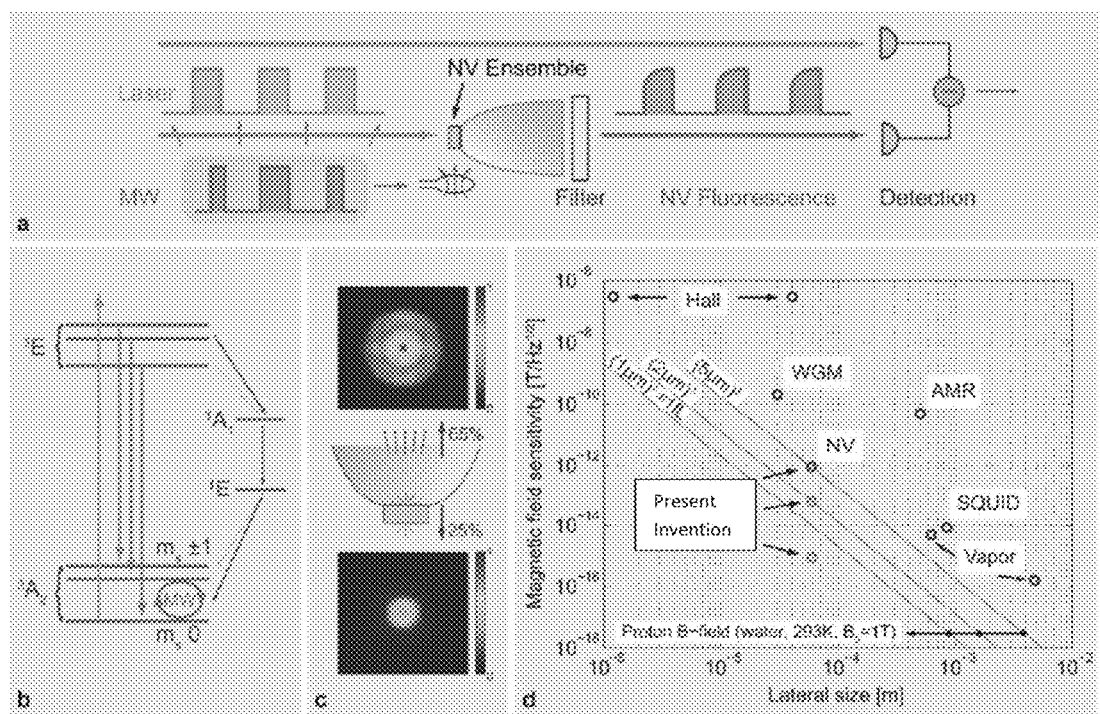
FIG. 1 illustrates various aspects of a nitrogen-vacancy (NV) diamond ensemble magnetometer including:
(a) A pulsed NV experiment: the NV ensemble is excited by 532 nm laser pulses; long-pass filtered fluorescence is collected with part of the exciting light on a difference photo detector; and microwave (MW) is used for NV spin manipulation.
(b) An NV energy level scheme showing manipulation of electron spin in the triplet ground state and spin state dependent fluorescence allows read out of the spin state.
(c) Fluorescence collection with a parabolic collector (simulation results).
(d) A comparison chart of magnetic field sensitivity versus sensor-to-sample distance for various available sensor techniques and the present invention with samples at room-temperature and remote detection including: vapour cells (optical readout); inductively coupled SQUIDs; anisotropic magnetoresistance sensors (AMR); whispering gallery mode resonator based sensors (WGM); Hall-sensors; and NV ensemble diamond sensor (the present invention). The X-coordinate in all cases is given as the radius of an assumed spherical detection volume calculated from stated volumes/sensor size in references. For comparison, straight lines indicate for various volumes the magnetic field from nuclear spins of protons in water at room-temperature and external magnetic field $B_o$=1T. The lowest line corresponds to the resolvable volume in optical confocal microscopy (1 femtoliter).

As indicated in the background section of this specification, NV defect centres in diamond are promising solid-state magnetometers. Single centres allow for high spatial resolution field imaging but are limited in their magnetic field sensitivity to around 10 nT/$\sqrt{Hz}$ at room temperature. Using defect centre ensembles sensitivity can be scaled as $\sqrt{N}$ where N is the number of defects. In the present specification, an ensemble of $10^{11}$ defect centres is utilized for sensing. By carefully eliminating all noise sources like laser intensity fluctuations, microwave amplitude and phase noise a photon shot noise limited field sensitivity of 0.9 pT/√Hz is achieved at room-temperature with an effective sensor volume of 8.5e-4 mm$^3$. The smallest field measured with the initial test device is 100 fT. While this denotes the best diamond magnetometer sensitivity to date, further improvements to the test device including the use of decoupling sequences and better diamond material will lead to fT/√Hz sensitivity.

In general, the sensitivity of a magnetic field measurement is given by $B_{min}(t)=\sigma(t)/(dS/dB)$, where the standard deviation of the sensor's signal $\sigma(t)$ is compared to the response of the system dS in a changing magnetic field dB. For the particular case of NV centres using a pulsed detection scheme with discrete readout steps the sensitivity is written as $$B_{min}(t) = \frac{\sigma_1}{\gamma \cdot A \cdot T_\varphi \cdot \sqrt{n}} \quad (1)$$

Here $n=t/T_{seq}$ is the number of field evaluations for a total measurement time t with $T_{seq}$, $\alpha_1$ and $T_\varphi$ the duration, the standard deviation and the phase accumulation time of a single field evaluation, respectively. Parameter A is the system-specific amplitude of the signal modulation.

Before dwelling on the accuracy of ensemble magnetometry it is instructive to analyse single spin measurements. The standard deviation of single spin sensor readouts $\sigma_1$ is dominated by shot noise of the fluorescence signal (essentially projection noise in photon number). Its ultimate limit however is spin projection noise due to the statistical nature of the quantum mechanical read out of the spin state. It is only reached by reducing the relative fluorescence shot noise below the spin projection noise limit. Steps towards this goal are for instance improved fluorescence detection efficiency by wave guiding effects as shown in Le Sage, D. et al. "Efficient photon detection from color centers in a diamond optical waveguide" *Phys. Rev. B* 85, 121202 (2012), repetitive readout or generally different detection schemes [Jiang, L. et al. "Repetitive Readout of a Single Electronic Spin via Quantum Logic with Nuclear Spin Ancillae" *Science* 326, 267-272 (2009); Neumann, P. et al. "Single-Shot Readout of a Single Nuclear Spin" *Science* 329, 542-544 (2010); Acosta, V. M. et al. "Broadband magnetometry by infrared-absorption detection of nitrogen-vacancy ensembles in diamond" *Appl. Phys. Lett.* 97, 174104 (2010); Jensen, K. et al. "Cavity-Enhanced Room-Temperature Magnetometry Using Absorption by Nitrogen-Vacancy Centers in Diamond" *Phys. Rev. Lett.* 112, 160802 (2014)]. Since both, fluorescence signal and spin projection, are sources of uncorrelated noise, sensitivity scales with √n the number of single sensor readouts over a wide range of measurement times.

We now turn to ensemble magnetometry. To further improve sensitivity, $\sigma_1$ is decreased with increasing fluorescence signal intensity when measuring on ensembles of NV centres. For independent emitters $\sigma_1$ should scale as $1/\sqrt{N}$ where N is the number of defects contributing to field measurement. Eventually, we calculate the spin projection limited magnetic field sensitivity as $$B_{QPN}(t) = \frac{1}{\gamma\sqrt{N \cdot t/T_{seq}} \cdot T_\varphi \cdot e^{-\delta(T_\varphi)}} \quad (2)$$

with $e^{-\delta(T_\varphi)}$ describing the decay of spin coherence and N the number of NV centers contributing to the signal. The equation is equivalent to the general derivation of Chin et al. [Chin, A. W., Huelga, S. F. & Plenio, M. B. Quantum Metrology in Non-Markovian Environments. *Phys. Rev. Lett.* 109, 233601 (2012)] for the case $T_{seq} \to T_\varphi$. In this case and for an exponential decay of spin coherence with a time constant $T_2$, the minimum of equation (2) is achieved for $T_\varphi=T_2/2$, which simplifies to $$B_{QPN}(t) = \frac{\sqrt{2e}}{\gamma\sqrt{NtT_2}} = 1.3 \cdot 10^{-11} R / \sqrt{NT_2}.$$

The test sensor utilized in the present work consists of a 0.9 ppm NV$^-$ HPHT-diamond, starting from 3 ppm nitrogen before conversion to NV by electron irradiation and has an optical thickness of 500 μm with <111> front planes. Fluorescence from the NV centres after pulsed excitation using a green laser is measured on one channel of a difference detector. The second channel of the detector is illuminated by part of the green excitation beam split from the exciting laser (FIG. 1a). Measurements shown were conducted at room temperature with a constant offset magnetic field of 46 Gauss along one NV orientation used for the measurements. The sensitivity of single centre magnetometry is limited by the number of detectable photons from a single defect being given by the photo-physics of the defect. In ensemble magnetometry, an additional challenge is to detect as much fluorescence photons as possible from a finite sample volume. As a result, different collection as well as absorption schemes have been proposed [Clevenson, H. et al. Broadband Magnetometry and Temperature Sensing with a Light Trapping Diamond Waveguide. *ArXiv*14065235 *Cond-Mat Physicsquant-Ph* (2014). at http://arxiv.org/abs/1406.5235]. In the present approach, fluorescence signal intensity from the NV centres is increased by using a parabolic shaped glass lens contacting one side of the diamond. As the étendue of a light source is conserved (for constant intensity), this structure essentially trades the initially large solid angle of fluorescence radiation against size of the emitting surface area of the structure. Simulations of the structure using commercial software show a collection efficiency higher than 60% without attempts for geometrical optimization of the diamond (FIG. 1c). Hence, the structure offers a collection efficiency comparable to the previously reported side detection approach with the additional advantage of a directed fluorescence output behind the structure. As a result, only one detector is needed for detection of the signal.

The present magnetic field measurement scheme comprises three steps. First, the NV sensor spins are polarised with a laser pulse. After initialization, a microwave preparation sequence is applied for B field measurement. The fluorescence signal is triggered and read out subsequently by launching another laser pulse. Microwave pulses are implemented using a coil antenna. Typical Rabi frequencies are on the order of 5 MHz.

For excitation, 400 mW of laser power with a diameter of 47 μm is focused onto the sample. The maximum intensity used is 25 kW/cm$^2$, which is below saturation (~100 kW/cm$^2$). The sample volume and hence the number N of defects contributing to the fluorescence signal is determined by the optical excitation and detection volume. Based on a measurement of the excitation area using a CCD camera and given the collection property of the parabolic lens, which is in first order spatially non-selective towards the fluorescence created, a detection volume of V=8.5e-4 mm$^3$ is calculated.

With a density of 0.9 ppm it is estimated that 1.4e11 NV centres contribute to the sensor signal.

From equation (1) an expected maximum sensitivity is estimated with $T_\phi=50$ µs of 100 fT/Hz$^{1/2}$ if values of single NV sensitivities are scaled with the aforementioned number of NV centres. From equation (2) the spin projection noise limit is calculated to be 6 fT/Hz$^{1/2}$ ($T_\phi$ is again set to 50 µs). This estimate relies on the assumption that the results of single readout steps show a normal distribution around a well-defined value (central limit theorem). This condition is usually met for measurements on single NV centres with comparably small numbers of total signal photons dominated by optical shot noise or spin projection noise—a frequency independent, uncorrelated white noise background. Ensemble magnetometry, however, dealing with much higher fluorescence intensities, is plagued by other, correlated and time-dependent noise sources. Since preparation and readout of the measurement relies on discrete preparation steps using laser and microwave, it is essential to analyse to what degree each of these sources influences the sensitivity and how to mitigate their impact.

An AC-magnetometry experiment has been performed as demonstrated previously [Balasubramanian, G. et al. Ultralong spin coherence time in isotopically engineered diamond. Nat. Mater. 8, 383-387 (2009)]. To this end, a spin-echo measurement with pulses $(\pi/2)_x-(\pi)_x-(\pi/2)_y$ is phase-locked to a sinusoidal ac magnetic field (see FIG. 2a). A phase accumulation time of $T_\phi=50$ µs is used and the overall single sequence length is $T_{seq}=160$ µs. The phase shift of the last $\pi/2$ pulse in the echo sequence assures maximum sensitivity already for smallest amplitude of the test field. By increasing the ac amplitude, the accumulated phase increases linearly with a concomitant sinusoidal fluorescence response. For the following investigations on the reproducibility of single sensor readouts and its scaling behaviour with averaging time, a point of maximum field sensitivity is chosen.

Figure 2:
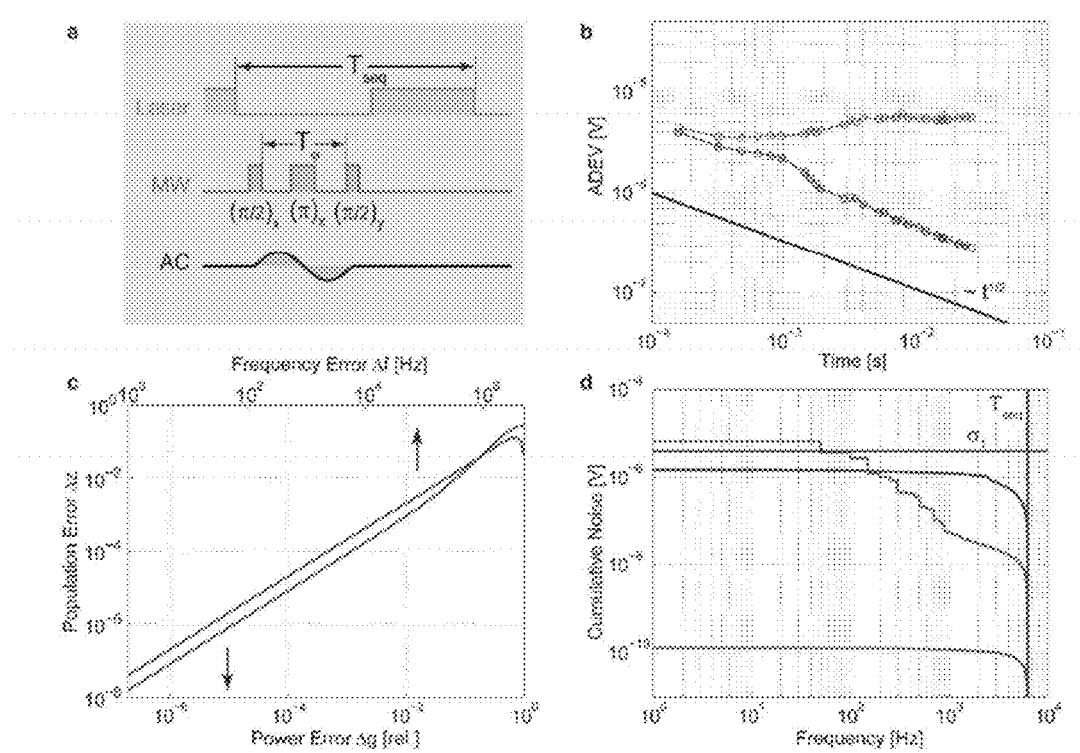
FIG. 2 illustrates the influence of non-white noise on magnetometer sensitivity including:
(a) AC magnetic field measurement scheme with pulsed sensor readout.
(b) Scaling of Allan deviation from Hahn Echo sequence with (green; upper line) and without (blue; middle line) microwave pulses. The slope of the black (lower) line indicates the desired scaling behaviour to approach a central limit. In case microwave pulses are applied scaling is worse than $\sqrt{t}$.
(c) Calculated spin state population error ($\Delta z$) after Hahn-Echo sequence over relative microwave power error $\Delta g$ (green; lower lone) and frequency error $\Delta f$ (red; upper line).
(d) Cumulative noise over sequence length $T_{seq}$ from high to low frequencies of laser (blue; middle line), microwave power (green; upper line) and microwave frequency (red; lower line). Measured deviation of single readout steps at indicated by a black horizontal line. Varying microwave power is expected to dominate the distribution of magnetic field evaluations on longer timescales. Therefore, results of field evaluations do not share a common central limit over time.

FIG. 2b shows the scaling of the Allan deviation of the readout signal of two different measurements. The upper curve corresponds to the spin-echo measurement described above. The second stems from an identical measurement but without applying microwave pulses in between laser readout pulses. While the Allan deviation may not be considered a valid estimator for the scaling of magnetic field sensitivity, it provides information on the correlation of consecutive measurements (here $t_{corr}$<100 ms) without being affected by overall (long-term) drift as in case of the standard deviation. As can be seen in the graph, once microwave pulses are applied sensitivity does scale worse than √n. No further improvement by averaging is achieved. Effects related to the implementation of the microwave sequence prevent favourable scaling of the readout signal. Note that the Allan deviation in conjunction with the applied spin echo sequence on short timescales suppresses effects of long-term drifts e.g. due to changes in temperature or magnetic background field. Thus, only external magnetic noise and variations of the implemented microwave sequence in the frequency range shown remain obvious culprits. The impact of microwave amplitude and frequency noise on measurement error is in general dependent on the particular choice of the microwave pulse sequence and noise frequency. For noise correlation times longer than the length of a single readout sequence ($T_{seq}$) an error in microwave amplitude or frequency can be taken to be constant throughout a single sequence. In this regime the signal error after a microwave pulse sequence due to a set of amplitude and frequency error parameters can be extracted from simulations of coherent spin rotations under the NV spin Hamiltonian [Cummins, H. K., Llewellyn, G. & Jones, J. A. "Tackling systematic errors in quantum logic gates with composite rotations" Phys. Rev. A 67, 042308 (2003); Breiland, W. G., Brenner, H. C. & Harris, C. B. "Coherence in multilevel systems. I. Coherence in excited states and its application to optically detected magnetic resonance in phosphorescent triplet states" J. Chem. Phys. 62, 3458-3475 (2008)]. FIG. 2c shows results for the scaling of signal error for two limiting cases: (1) Scaling with the relative microwave power error $\Delta g$ ($\Delta f=0$) and (2) Scaling with the absolute microwave frequency error $\Delta f$ ($\Delta g=0$). Both quantities show a linear scaling behaviour in the relevant parameter range.

Amplitude and phase noise of the microwave system was measured using established cross-correlation techniques. Both are given for frequencies f below the inverse sequence length ($1/T_{seq}$) in FIG. 2d (cumulative root sum of squares from $1/T_{seq}$ to f). The optical noise is given in the same way and the Allan deviation of single sequence readouts is indicated as horizontal black line. Three results can be inferred from the graph. First, the influence of microwave frequency noise on scaling of the signal is negligible. Secondly, the optical low frequency noise (f<$1/T_{seq}$) is well below the mutual deviation range of single sequence readouts. This enables the preferential scaling with √n for the case where no microwave pulses were applied. Finally, the effect of microwave amplitude noise is small on the timescale of single readout steps but increases towards longer timescales and exceeds the level of deviation of single readout steps. In the latter case, scaling of the measurement is worse than √n as the central limit theorem does not apply. The centre of the distribution of measurement values rather drifts around a new, larger range now being dominated by microwave amplitude noise. In essence, varying microwave amplitudes lead to improper conversion of field to signal amplitude that prevents a decrease of the measurement error with increasing averaging time.

Figure 3:
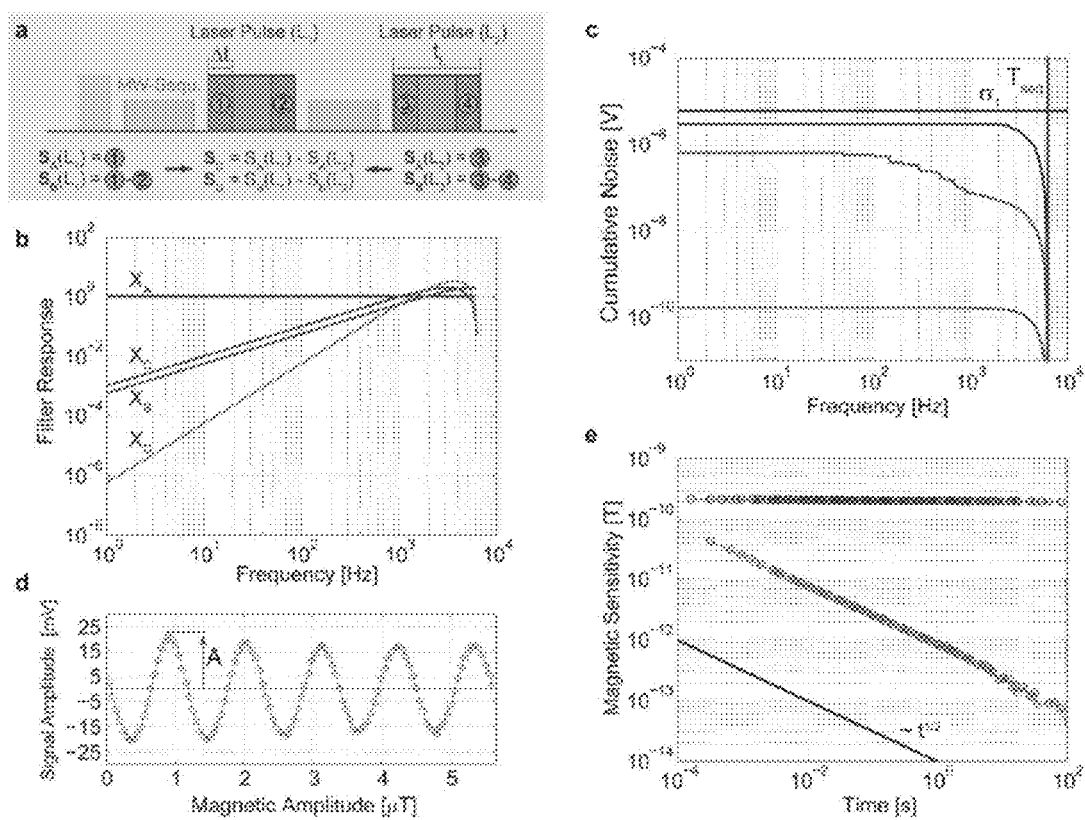
FIG. 3 illustrates sequence filter and sensitivity scaling including:
(a) Measurement signals ($S_A$-$S_D$) represent different ways of taking the signal from the sensor.
(b) Corresponding sequence filter functions resulting from signals $S_A$-$S_D$.
(c) Cumulative, sequence filtered noise of laser (blue; top line), microwave power (green; middle line) and microwave frequency (red; lower line) for signal $S_D$. The black, horizontal line indicates single sequence readout deviation ($\sigma_1$). $\sigma_1$ remains the dominant contribution within the timescale shown.
(d) Magnetic measurement of test field with varying field amplitude retrieves sensor response A.
(e) Scaling of magnetic sensitivity (standard deviation over time) of signal $S_B$ (blue; upper line) and $S_D$ (green; middle line). The slope of the black (lower) line indicates the aspired scaling behaviour with $\sqrt{t}$.

One way to reduce the impact of inaccurate microwave pulses on scaling of the readout signal is to reference the signal on a timescale shorter than the characteristic correlation time of the noise. Owing to the photo-physical dynamics of the NV centre, the spin signal is typically read out in the first part of a laser pulse. It is common practice to reference this signal ('1' in FIG. 3a) to the steady state fluorescence level after re-initialization of the NV centres at the end of the laser pulse ('2' in FIG. 3a) yielding the measurement signal SB. Implicitly, this procedure mitigates optical noise with a correlation time longer than the laser pulse length (100 µs). Effectively, it implements a filter $X_B$ for optical noise frequencies lower than the inverse laser pulse length, i.e. 10 kHz. The filter $X_B$ related to signal $S_B$ can be calculated by the Fourier transform of the respective signal integration window $C_B$ by $$X_B(\omega) = \left| \int_{-\infty}^{\infty} dt\, e^{-i\omega t} C_B(t) \right| \quad (3a)$$

$$C_B(t) = \begin{cases} 1, & t \in [0, \Delta t] \\ -1, & t \in [t_L - \Delta t, t_L] \\ 0, & \text{otherwise} \end{cases} \quad (3b)$$

with the length of the laser pulse $t_L$ and the integration time $\Delta t$ (see also FIG. 3a). It is stressed that this filter is different from (1) filter functions implemented with microwave pulses with the intention to shape the response of NV centres towards a certain band of magnetic signal frequencies [Naydenov, B. et al. "Dynamical decoupling of a single-electron spin at room temperature" *Phys. Rev. B* 83, (2011); Lange, G. de, Wang, Z. H., Ristè, D., Dobrovitski, V. V. & Hanson, R. "Universal dynamical decoupling of a single solid-state spin from a spin bath" *Science* 330, 60-63 (2010)] and (2) filter functions related to data (post-) processing (e.g. to improve the signal-to-noise-ratio). The filter referred to here is an intrinsic part of the measurement system based on the fact that discrete, non-continuous time frames are measured.

While the described filter only affects the laser induced correlated fluctuations of the signal, a reference for the state preparation with microwave pulses can be established likewise by introducing a second preparation and readout sequence as shown in FIG. 3a for signal $S_D$. To understand the impact of this procedure the filter transmission for the four different ways of measuring the NV signal ($S_A$ to $S_D$) is calculated as shown in FIG. 3a. Signal $S_A$ does not contain any referencing. $S_B$, as explained above, implements one filtering step for the optical signal on the timescale of the laser pulse length. $S_C$ results in one referencing step for both optical and microwave-related noise on the timescale of the sequence length. Finally $S_D$ gives two referencing steps versus the optical part and one for the microwave contribution.

Calculation of filters $X_{A/C/D}$ is analogous to $X_B$ and the calculated filter responses are given in FIG. 3b for the same set of parameters used for the measurements from above $t_L=100$ µs, $\Delta t=10$ µs and $T_{seq}=160$ µs. The calculation of the filter transmission is herein restricted to noise frequencies in the low frequency regime up to the range of $1/T_{seq}$. Note that the response of the measured signal corresponding to the implementation of the signal measurement procedure $S_D$ results in filter $X_D$ for optical noise because of two referencing steps. It results in filter $X_C$ for the microwave noise contributions since state preparation by microwave only affects the signal in the first part of the laser pulses. With the calculated filter responses, the cumulative noise (root sum of squares) is given weighted with the respective filters for microwave components and the optical part corresponding to the measurement procedure $S_D$ from two consecutive readouts (FIG. 3c). The calculation shows that referencing the signal in this way very efficiently suppresses low frequency noise components. The contribution of microwave amplitude noise is kept below the limit set by the deviation of single readout steps.

Next, the ac-magnetometry sequence is repeated as described above and in FIG. 2a, however, measuring signals $S_B$ and $S_D$. After varying the strength of the magnetic test field to retrieve the amplitude of the sensor response (FIG. 3d) the actual ac field is switched off to (1) reach the working point of highest sensitivity and (2) exclude additional noise sources from the ac signal itself. The scaling of the sensitivity, given here as the standard deviation for the two signals $S_B$ and $S_D$, is shown in FIG. 3e. In case of signal $S_B$ (blue; top line) increased averaging time does not improve the measurement result. Signal $S_D$ (green; middle line) shows a scaling with $1/\sqrt{t}$ where t is the total signal averaging time and reaches a sensitivity of 0.9 pT/Hz$^{1/2}$. For longer measurement time an absolute sensitivity of around 100 fT or lower is achieved.

The sensitivity shown marks an improvement by three orders of magnitude in magnetic field sensitivity when compared to previously published NV diamond related results. Secondly, it has been shown for the first time a $\sqrt{t}$ scaling behaviour in NV ensemble magnetometry, being a requirement for strategies to improve sensitivity. Moreover, the scaling behaviour shows that the measurement is so far limited neither by temperature variation nor by external in-band magnetic noise. It has been found that the standard deviation of the signal $S_D$ is by a factor of 5.3 above the fluorescence shot noise level that one would expect for a simple readout of the repolarization signal only ($S_A$). This agrees well with the expected increase in uncorrelated noise. While correlated noise is largely suppressed with the procedures described, uncorrelated noise increases by a factor $\sqrt{2}$ with every referencing step implemented if one assumes identical noise density for the uncorrelated noise of the two signals referenced. Since 3 referencing steps have been introduced (exciting laser against fluorescence and two in measurement procedure $S_D$) and an additional factor for doubling the measurement time, the contribution of uncorrelated noise is effectively increased by $\sqrt{24}=4$. Concluding, implemented a self-referencing measurement of a single sensor at different times, instead of mutual referencing of two sensors at the same time, can yield an improvement of $\sqrt{23}$.

When compared to the sensitivity extrapolation from measurements on single NV centres from equation (1), a deviation by one order of magnitude is found. This discrepancy is resolved by accounting for the reduction in contrast when measuring on one of four NV-axes and the increase in uncorrelated noise by 5.3 mentioned before. The sensitivity of measurements on NV ensembles can even exceed the projection derived from single NV measurements due to improved fluorescence collection efficiency. Finally, it is emphasized that the implementation of the measurement procedure $S_D$ except for a decrease in measurement rate does not impose any additional restrictions. As control of the ac-magnetic field is required (e.g. switch off in every second measurement, in-phase with spin echo sequence), in real measurements the source of ac magnetic field needs to be controlled (e.g. invoked flips of electron or nuclear spins to be measured) [Neumann, P. et al. Quantum register based on coupled electron spins in a room-temperature solid. *Nat. Phys.* 6, 249-253 (2010); Mamin, H. J. et al. Nanoscale Nuclear Magnetic Resonance with a Nitrogen-Vacancy Spin Sensor. *Science* 339, 557-560 (2013)].

The present specification highlights the role of technical noise and its mitigation to sensitivity scaling in NV ensemble magnetometry. By reducing the influence of non-white noise contributions over an extended frequency range a $\sqrt{t}$ scaling in sensitivity is achieved close to the photon shot noise limit, finally reaching sub pT/$\sqrt{Hz}$ sensitivity for a sensor volume of 8.5e-4 mm$^3$. Referring to FIG. 1d, this places the current sensor in terms of sensitivity per volume among state-of-the-art sensor implementations. Different strategies are conceived to further improve the magnetic sensitivity. In Pham, L. M. et al. [Enhanced solid-state multispin metrology using dynamical decoupling. *Phys. Rev. B* 86, 045214 (2012)] higher order dynamical decoupling sequences were applied to NV ensembles yielding a phase memory time of 2 ms, which is the limit set by longitudinal spin relaxation of NV centres at room temperature. With the experimental settings described here, with a similar amount of NV centres and identical efficiency of the filters applied, this would yield a sensitivity of 40 fT/$\sqrt{Hz}$. The latter is still almost two orders of magnitude above the limit set by the spin projection noise (0.9 fT/√Hz). This value itself allows for detection of proton spins in a microscopically resolvable volume in less than one second. Nuclear spin assisted repetitive readout, infrared absorption based readout or enhancement by optical cavities are strategies which can be applied to reach the projection noise limit.

While this invention has been particularly shown and described with reference to embodiments, it will be understood to those skilled in the art that various changes in form and detail may be made without departing from the scope of the invention as defined by the appending claims. Additional information about the methods applied herein is provided below.

Allan Deviation

The (non-overlapping) Allan deviation (T) of a set of data samples $S=[S_1, S_2, \ldots, S_n]$ with sample spacing t' is defined for a given time interval T by:

$$\sigma_A^2(\tau) = \frac{1}{2}\langle (x_{i+1} - x_i)^2 \rangle_\tau \qquad (4)$$

Here, $x_i$ denotes the mean ($\langle \cdot \rangle$) over the subset of m=τ/t' successive elements of S within the $i^{th}$ τ-interval:

$$x_i = \langle [S_{(i-1)m+1}, S_{(i-1)m+2}, \ldots, S_{i \cdot m}] \rangle \qquad (5)$$

AC Magnetometry Sequence

For AC magnetometry the most basic sequence is applied, namely a Hahn echo measurement $((\pi/2)-(\pi)-(\pi/2))$. Hence, a microwave π/2 pulse creates a spin superposition state followed by two equal free evolution times $T_\phi/2$ separated by a π pulse. The AC signal has the frequency $1/T_\phi$ and is in phase with the π pulse (e.g. the zero crossing of a sine wave coincides with the π pulse) in order to yield highest field sensitivity. The accumulated phase of the sensing spins is proportional to the field strength ($\phi=\gamma \cdot B \cdot T_\phi$). Finally, a second π/2 pulse is applied to convert phase into a detectable spin population difference (e.g. the population of spin projection $m_S=0$, $p_{mS=0}=\frac{1}{2}(1+\cos \phi)$). Highest sensitivity is achieved around the point of equal spin state population (i.e. $p_{mS=0}=0.5$). Adjusting the phase φ of the final microwave pulse assures the optimal working point for arbitrary field strengths (i.e. $p_{mS=0}=\frac{1}{2}(1+\cos(\omega+\phi)))$. Consequently, for highest sensitivity to magnetic fields around zero amplitude the final pulse has to be phase shifted by φ=90°. Thus, the Hahn echo measurement sequence changes to $(\pi/2)_x-(\pi)_y$. In addition, high dynamic range magnetometry can be applied to remove field ambiguities and at the same time retain highest sensitivity [Said, R., Berry, D. & Twamley, J. Nanoscale magnetometry using a single-spin system in diamond. *Phys. Rev. B* 83, 125410 (2011); Waldherr, G. et al. High-dynamic-range magnetometry with a single nuclear spin in diamond. *Nat. Nanotechnol.* 7, 105-108 (2011)].

Error Scaling with Microwave Amplitude and Frequency

In order to estimate the impact of microwave pulse errors on the measurement the population difference is calculated between the target state (ideal pulses) and the outcome of a pulse sequence with constant error in microwave frequency and microwave power throughout a sequence (Hahn echo). Successive coherent spin rotations are calculated using the NV spin Hamiltonian:

$$H=DS_z^2+B_z(\gamma S_z+\gamma_n I_z)+AS_z I_z \qquad (6)$$

D=2.87 GHz is the zero-field splitting, $\gamma/2\pi$=28.7 GHz/T is the gyromagnetic ratio of the NV-electron spin, $\gamma_n 2\pi$=3.08 MHz/T the nuclear gyromagnetic ratio of $^{14}$N and A=2.16 MHz is the hyperfine coupling between NV-electron and $^{14}$N-nuclear spin. $S_z$ and $I_z$ are the electron and nuclear spin projection operators respectively.

Filter Functions

Explicit evaluation of equations 3a-b yields the filter function $X_B$:

$$X_B = \sqrt{|2/\omega^2 \cdot [(2 - 2 \cdot \cos\omega\Delta t + \cos\omega(t_L - 2\Delta t) + \cos\omega t_L - 2 \cdot \cos\omega(t_L - \Delta t)]|}$$

Filter functions $X_{A/C/D}$ are calculated in an analogous way using the corresponding signal integration windows $C_{A/C/D}$.

The invention claimed is:

1. A magnetometer comprising:
    a sensor formed of diamond material and comprising a plurality of spin centres;
    a microwave source configured to subject the plurality of spin centres to microwave pulses;
    a light source configured to subject the plurality of spin centres to light pulses; and
    a detector configured to detect a fluorescent output signal emitted from the plurality of spin centres,
    wherein the magnetometer is configured to integrate the fluorescent output signal over a signal averaging time and process the fluorescent output signal such that a standard deviation of the fluorescent output signal decreases with the square root of the signal averaging time over a time period which spans at least two orders of magnitude in the signal averaging time to achieve a standard deviation of less than 100 picotesla.

2. The magnetometer according to claim 1, wherein the standard deviation of the fluorescent output signal decreases linearly with the square root of the signal averaging time.

3. The magnetometer according to claim 1, wherein the standard deviation of the fluorescent output signal decreases with the square root of the signal averaging time over a time period which spans at least three orders of magnitude in the signal averaging time.

4. The magnetometer according to claim 1, wherein the standard deviation of the fluorescent output signal decreases with the square root of the signal averaging time over a time period which spans at least four orders of magnitude in the signal averaging time.

5. The magnetometer according to claim 1, wherein the standard deviation of the fluorescent output signal decreases with the square root of the signal averaging time over a time period which spans at least five orders of magnitude in the signal averaging time.

6. The magnetometer according to claim 1, wherein the standard deviation of the fluorescent output signal decreases with the square root of the signal averaging time over a time period which spans at least six orders of magnitude in the signal averaging time.

7. The magnetometer according to claim 1, wherein a standard deviation of less than 10 picotesla is achieved.

8. The magnetometer according to claim 1, wherein a standard deviation of less than 1 picotesla is achieved.

9. The magnetometer according to claim 1,
wherein a standard deviation of less than 0.1 picotesla is achieved.

10. The magnetometer according to claim 1,
wherein a standard deviation of less than 0.01 picotesla is achieved.

11. The magnetometer according to claim 1,
wherein a standard deviation of less than 1 femtotesla is achieved.

12. The magnetometer according to claim 1,
wherein the signal averaging time is at least 0.1 seconds and the standard deviation of the fluorescent output signal decreases with the square root of the signal averaging time over this time period.

13. The magnetometer according to claim 1,
wherein the signal averaging time is at least 1 second and the standard deviation of the fluorescent output signal decreases with the square root of the signal averaging time over this time period.

14. The magnetometer according to claim 1,
wherein the signal averaging time is at least 10 seconds and the standard deviation of the fluorescent output signal decreases with the square root of the signal averaging time over this time period.

15. The magnetometer according to claim 1,
wherein the signal averaging time is at least 100 seconds and the standard deviation of the fluorescent output signal decreases with the square root of the signal averaging time over this time period.

16. The magnetometer according to claim 1,
wherein the magnetometer is configured to process the fluorescent output signal by filtering both optical and microwave noise to produce a filtered signal $S_D$ having a magnetic sensitivity expressed as the standard deviation over time which scales as a function of the square root of the signal averaging time.

17. The magnetometer according to claim 15,
wherein the magnetometer is configured to filter both optical and microwave noise by combining multiple pulse referencing steps to determine the filtered signal $S_D$.

18. The magnetometer according to claim 15,
wherein the magnetometer is configured to measure the fluorescent output signal over a plurality of discrete, non-continuous time frames and combine the plurality of discrete, non-continuous measurements to generate the filtered signal $S_D$.

19. The magnetometer according to claim 15,
wherein the filtered signal $S_D$ is generated by taking a read-out measurement during a first part of a laser pulse, taking a reference measurement during a second part of the laser pulse, repeating the read-out and reference measurements for a subsequent laser pulse, and then calculating the filtered signal $S_D$ using the read-out measurements and the reference measurements from both laser pulses thus accounting for both laser pulse variations and also microwave variations between the laser pulses.

20. The magnetometer according to claim 1,
wherein the spin centres are negatively charged nitrogen-vacancy ($NV^-$) spin centres.

* * * * *